US00PP23566P2

(12) United States Plant Patent
Nishikawa

(10) Patent No.: US PP23,566 P2
(45) Date of Patent: Apr. 23, 2013

(54) ***DELOSPERMA* PLANT 'JEWEL OF DESERT PERIDOT'**

(50) Latin Name: *Delosperma cooperi*
Varietal Denomination: Jewel of Desert Peridot

(75) Inventor: Koichiro Nishikawa, Quito (EC)

(73) Assignee: Ron Van Dijkconsultancy B V, Boskoop (NL)

( * ) Notice: Subject to any disclaimer, the term of this patent is extended or adjusted under 35 U.S.C. 154(b) by 0 days.

(21) Appl. No.: 13/199,815

(22) Filed: Sep. 9, 2011

(51) Int. Cl.
*A01H 5/00* (2006.01)

(52) U.S. Cl. ..... Plt./422

(58) Field of Classification Search ..... Plt./422
See application file for complete search history.

*Primary Examiner* — Howard Locker
(74) *Attorney, Agent, or Firm* — Penny J. Aguirre

(57) ABSTRACT

A new cultivar of *Delosperma* plant, 'Jewel of Desert Peridot', characterized by its compact and very horizontal plant habit, its high heat tolerance its relatively small leaves, its very floriferous and long blooming flowering habit, and its flowers that are yellow in color with white centers and yellow anthers.

2 Drawing Sheets

Botanical classification: *Delosperma cooperi.*
Variety denomination: 'Jewel of Desert Peridot'.

CROSS REFERENCE TO RELATED APPLICATIONS

This application is co-pending with a U.S. Plant Patent Applications filed for plants derived from the same breeding program that are entitled *Delosperma* Plant Named 'Jewel of Desert 'Rosequartz' (U.S. Plant patent application Ser. No. 13/199,787), *Delosperma* Plant Named 'Jewel of Desert Moon Stone' (U.S. Plant patent application Ser. No. 13/199,823), *Delosperma* Plant Named 'Jewel of Desert Topaz' (U.S. Plant patent application Ser. No. 13/199,826), *Delosperma* Plant Named 'Jewel of Desert Ruby' (U.S. Plant patent application Ser. No. 13/199,812), and *Delosperma* Plant Named 'Jewel of Desert Garnet' (U.S. Plant patent application Ser. No. 13/199,846).

BACKGROUND OF THE INVENTION

The present invention relates to a new and distinct cultivar of *Delosperma* plant, botanically known as *Delosperma cooperi* 'Jewel of Desert Peridot' and will be referred to hereinafter by its cultivar name, 'Jewel of Desert Peridot'. The new cultivar of *Delosperma* is a herbaceous perennial grown for container and landscape use.

The new cultivar was derived from a controlled breeding program conducted by the Inventor in Ichinimiya-City, Aichi-Pref, Japan. The overall purpose of the breeding program was to develop new cultivars of *Delosperma* plants with low-growing and well-spreading growth habits combined with long flowering periods and a unique range of flower colors.

'Jewel of Desert Peridot' was selected in the Inventor's trial garden in November 2006 as a single unique plant from amongst the seedlings derived from self-crossing an unnamed plant from the Inventor's breeding program in 2005. The Inventor's reference number for the parent plant is 2005-1.

Asexual propagation of the new cultivar was first accomplished by softwood cuttings in 2009 by the Inventor in Ichinimiya-City, Aichi-Pref, Japan. Propagation by softwood cuttings has shown that the unique features of the new cultivar are stable and reproduced true to type in successive generations.

SUMMARY OF THE INVENTION

The following traits have been repeatedly observed and are determined to be the characteristics of the new cultivar. These attributes in combination distinguish 'Jewel of Desert Peridot' as a unique cultivar of *Delosperma.*

1. 'Jewel of Desert Peridot' exhibits a compact and very horizontal plant habit.
2. 'Jewel of Desert Peridot' exhibits relatively small leaves.
3. 'Jewel of Desert Peridot' exhibits a very floriferous and long blooming flowering habit.
4. 'Jewel of Desert Peridot' is highly heat tolerant.
5. 'Jewel of Desert Peridot' exhibits flowers that are yellow in color with white centers and yellow anthers.

The parent plant of 'Jewel of Desert Peridot', Ref. No. 2005-1, differs from 'Jewel of Desert Peridot' in having a more upright (less horizontal) plant habit, in blooming for a shorter time period, and in having flowers that are pink in color and lack white centers. 'Jewel of Desert Peridot' can be most closely compared to the cultivar 'Reiko' (not patented), which is similar to 'Jewel of Desert Peridot' in having a horizontal plant habit. 'Reiko' differs from 'Jewel of Desert Peridot' in having larger leaves, purple flowers, in blooming for a shorter period of time, and in being less heat tolerant.

'Jewel of Desert Peridot' can also be compared to cultivars with co-pending patent applications from the same breeding program that differ from 'Jewel of Desert Peridot' most significantly in flower color:

'Jewel of Desert Moon Stone' has white flowers with yellow anthers.

'Jewel of Desert Topaz' has yellow-orange flowers with red petal tips, white-light purple centers, and yellow anthers.

'Jewel of Desert Rosequartz' has light pink flowers with white centers and yellow anthers.

'Jewel of Desert Ruby' has red flowers with deep pink and white centers and yellow anthers.

'Jewel of Desert Garnet' has red-orange flowers with pink centers and yellow anthers.

BRIEF DESCRIPTION OF THE DRAWINGS

The accompanying colored photographs illustrate the overall appearance and distinct characteristics of the new *Delosperma*. The plant in the photograph is 3 months in age as grown in a 7-cm container in a unheated greenhouse in Noordwijkerhout, The Netherlands.

The photograph in FIG. 1 provides a side view of 'Jewel of Desert Peridot' in bloom.

Figure 1:
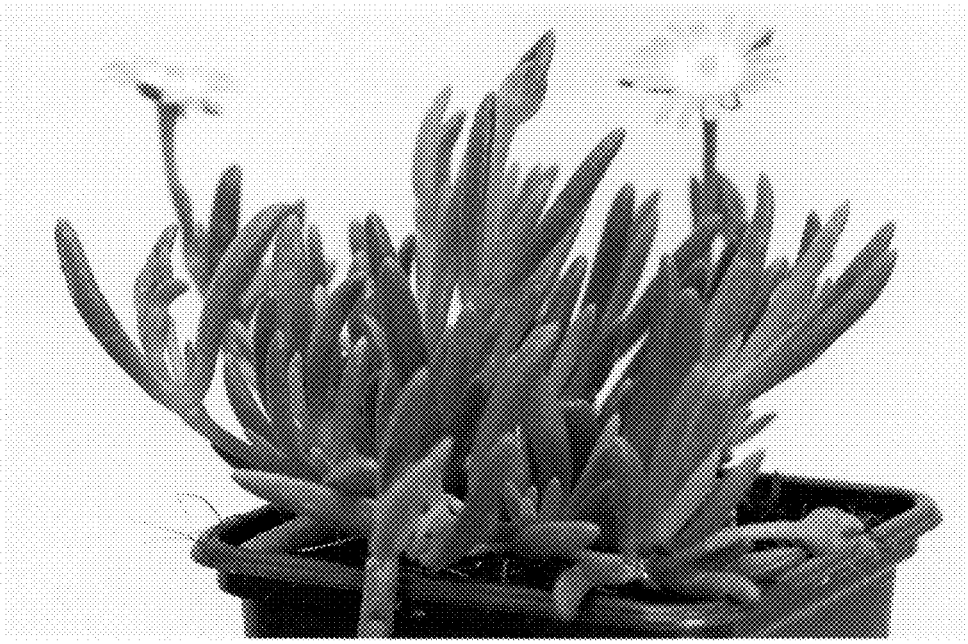
Figure 2:
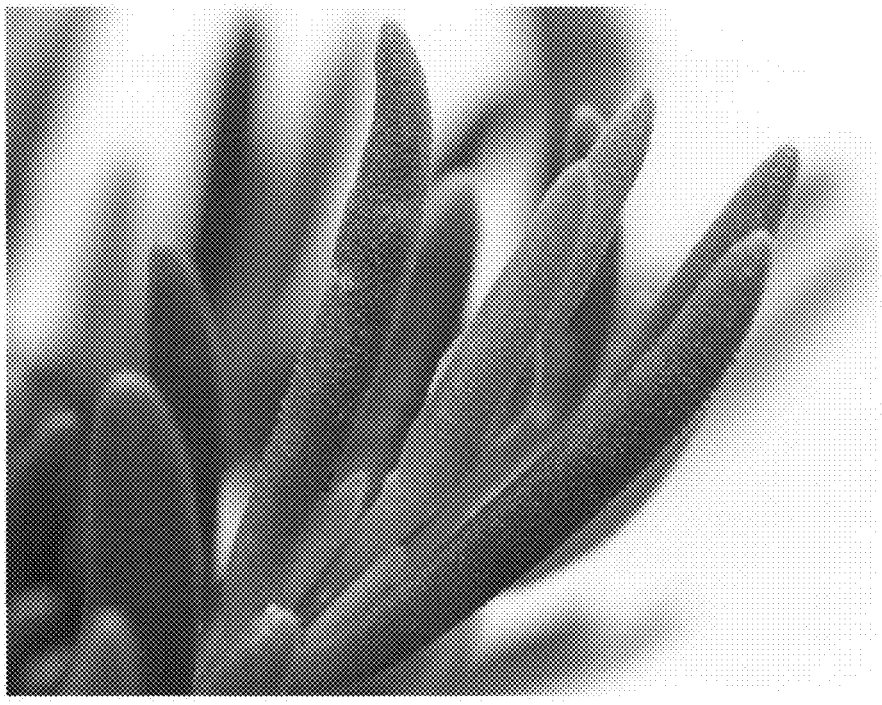

The photograph in FIG. 2 provides a close-up view of the foliage of 'Jewel of Desert Peridot'.

Figure 3:
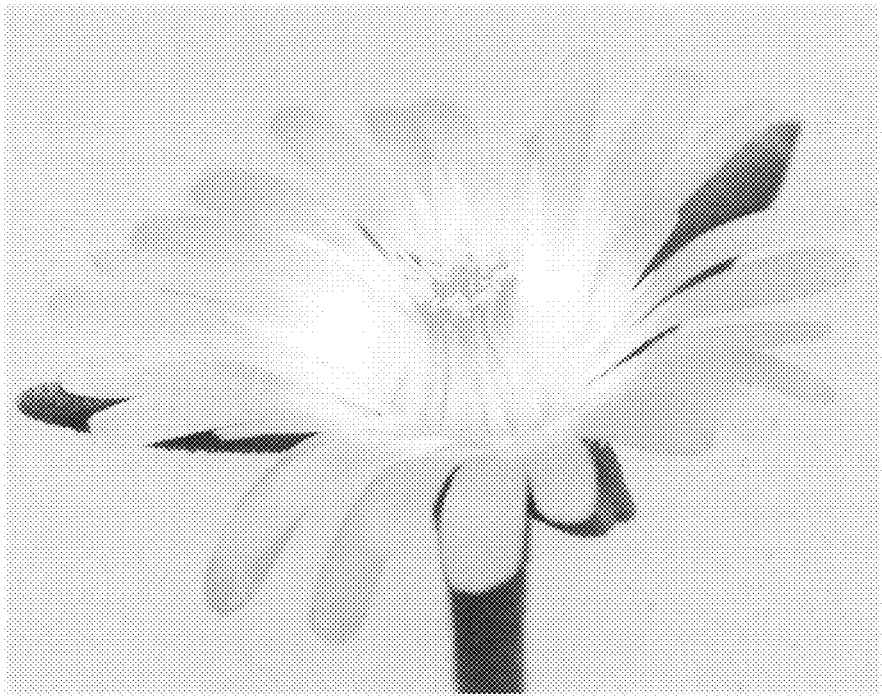

The photograph in FIG. 3 provides a close-up view of a flower of 'Jewel of Desert Peridot'. The colors in the photographs may differ slightly from the color values cited in the detailed botanical description, which accurately describe the colors of the new *Delosperma*.

DETAILED BOTANICAL DESCRIPTION

The following is a detailed description of three month-old plants of the new cultivar as grown in 7-cm containers in a unheated greenhouse in Noordwijkerhout, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Mid April to mid September in Noordwijkerhout, The Netherlands.

*Plant type*.—Herbaceous perennial.

*Plant habit*.—Compact, well-spreading, horizontal.

*Height and spread*.—Reaches about 7.5 cm in height and about 15.7 cm in diameter with mature plants reaching up to 10 cm in height and 30 cm in spread.

*Cold hardiness*.—Observed to be hardy to U.S.D.A. Zone 7.

*Environmental stresses*.—Highly heat tolerant.

*Diseases*.—No more susceptible or resistant to diseases than other *Delosperma cooperi* varieties, diseases are typically not a problem for *Delosperma cooperi*, except when grown with too much moisture.

*Root description*.—Fibrous roots.

*Propagation*.—Softwood cuttings.

*Growth habit*.—Moderately vigorous.

Stem description:

*Shape*.—Round.

*Stem color*.—182D with older stems a blend of 145C and 150D.

*Stem size*.—Lateral branches; an average of 3.4 cm in length and 2 mm in diameter.

*Internode length*.—An average of 1.5 cm.

*Stem substance*.—Succulent.

*Stem surface*.—Moderately glossy, sparsely to moderately pubescent with very short glandular hairs; an average of 0.2 mm in length and about 155C in color.

*Branching habit*.—Basal branching with an average of 11 lateral branches per stem.

Foliage description:

*Leaf shape*.—Ligulate, triangular in diameter.

*Leaf substance*.—Succulent.

*Leaf division*.—Simple.

*Leaf base*.—Cuneate.

*Leaf apex*.—Acute.

*Leaf venation*.—No veins visible.

*Leaf margins*.—Entire.

*Leaf arrangement*.—Opposite.

*Leaf surface* (*upper and lower surface*).—Slightly glossy, slightly pubescent with very short glandular hairs; an average of 0.2 mm in length, 155C in color.

*Leaf color*.—Young upper and lower surface; 143A, base 143B, mature upper and lower surface; 137B.

*Leaf size*.—About 3.1 cm in length and 4 mm in width.

*Leaf quantity*.—Average of 6 (3 pairs) per lateral branch.

*Leaf attachment*.—Sessile.

Inflorescence description:

*Inflorescence type*.—Flowers solitary.

*Flower number*.—An average of 2 per lateral stem, 20 per plant.

*Flower fragrance*.—Moderately faint, sweet and pleasant.

*Flower aspect*.—Outward to upright.

*Flower longevity*.—A few days.

*Flower type*.—Single.

*Flower size*.—Average of 2.4 cm in diameter and 9 mm in depth.

*Flower buds*.—Broadly ovate to oblong in shape, an average of 1.0 cm in length and 5 mm in diameter, color; 137B, base 143C.

*Calyx*.—Rotate in shape, average of 5 mm in depth and 1.7 cm in diameter.

*Sepals*.—4, rotate, ovate in shape, margin entire, an average of 7 mm in length and 2.5 mm in width, broadly acute apex, broadly cuneate base, upper and lower surface is smooth and dull, color young upper and lower surface; 137B, base 143C, color mature upper and lower surface; 137A.

*Petals*.—An average of 44 per flower, rotate and slightly curved, narrowly oblanceolate in shape, upper and lower surface is smooth and moderately glossy, margin entire, apex obtuse, base cuneate, an average of 1.0 cm in length and 1.5 mm in width, color; opening flowers upper surface; 12A, base NN155D, opening flowers lower surface; a blend of 9A and 12A, base NN155D, fully opened flower upper surface; 12A, base NN155D, fully opened flower lower surface; a blend of 9A and 12A, base NN155D, fading upper surface; 12D, base NN155D fading lower surface; 12CA, base NN155D.

*Petaloids*.—An average of 30 per flower, rotate and near vertical surrounding stamens, lanceolate in shape, upper and lower surface is moderately to highly glossy, margin entire, apex obtuse, base truncate, an average of 4 mm in length and 1 mm in width, color; mature and immature surfaces; NN155B, non fading.

*Peduncle*.—Average of 3.4 cm in length and 1.5 mm in diameter, straight on top of lateral branch at 0°, 144C in color, surface moderately glossy, sparsely to moderately pubescent with very short glandular hairs.

Reproductive organs:

*Pistils*.—About 5, triangular shaped stigma, style and stigma (not distinguishable) are an average of 2 mm in length and 144B in color, ovary is 143C in color.

*Stamens*.—Average 60, anthers are dorsifixed and narrowly oblong in shape, an average of 0.5 mm in diameter and 13A in color, filaments are 2.5 mm in length and NN155D in color, pollen is moderate in quantity and 13A in color.

*Fruit*.—Fruit and seed production was not observed under the conditions tested.

It is claimed:

1. A new and distinct variety of *Delosperma* plant named 'Jewel of Desert Peridot' as described and illustrated herein.

* * * * *